United States Patent [19]

Segall et al.

[11] Patent Number: 5,070,105

[45] Date of Patent: Dec. 3, 1991

[54] STABILIZED ANTIMICROBIAL COMPOSITIONS

[76] Inventors: Jeanne Segall, 3 Shimshon Street; Leonard M. Shorr, 39 Hapalmach Street, both of Haifa, Israel

[21] Appl. No.: 346,724

[22] Filed: May 3, 1989

Related U.S. Application Data

[63] Continuation-in-part of Ser. No. 54,217, May 26, 1987, abandoned, which is a continuation of Ser. No. 713,783, Mar. 20, 1985, abandoned, which is a continuation of Ser. No. 551,415, Nov. 14, 1983, abandoned.

[30] Foreign Application Priority Data

Nov. 17, 1982 [IL] Israel ........................................ 67282

[51] Int. Cl.$^5$ ............................................ A01N 37/18
[52] U.S. Cl. .................................... 514/626; 514/772; 514/788; 514/970
[58] Field of Search ............... 514/528, 626, 970, 788, 514/772

[56] References Cited

U.S. PATENT DOCUMENTS

| | | | |
|---|---|---|---|
| 4,163,795 | 8/1979 | Burk | 514/528 |
| 4,163,796 | 8/1979 | Burk | 514/528 |
| 4,163,797 | 8/1979 | Burk et al. | 514/528 |
| 4,163,798 | 8/1979 | Burk et al. | 514/528 |
| 4,190,668 | 2/1980 | Burk et al. | 514/528 |

OTHER PUBLICATIONS

Chem. Abstracts 66:76585c (1967).
Chem. Abstracts 76:15560a (1972).
Chem. Abstracts 77:1832z (1972).
Chem. Abstracts 78:86930y (1973).
Chem. Abstracts 78:112063g (1973).

*Primary Examiner*—Frederick E. Waddell
*Assistant Examiner*—Raymond J. Henley, III
*Attorney, Agent, or Firm*—Burns, Doane, Swecker & Mathis

[57] ABSTRACT

Stabilized antimicrobial compositions containing an antimicrobial amount of 2,2-dibromo-3-nitrilopropionamide in water miscible organic solvents. The stabilizer used is selected from chain-breaking antioxidants of the phenolic or amine type in an amount in the range of 0.001% to 0.5% by weight of the composition. Typical examples of stabilizers are: 2,6-di-tert-butyl-p-cresol; 4,4'-bis-(2,6-di-tert-butylphenol); 2,6-di-tert-butyl-α-methoxy-p-cresol and N-phenyl-β-naphthylamine. The antimicrobial compositions also contain one or more water miscible organic solvents selected from those known in the art, in which the 2,2-dibromo-3-nitrilopropionamide is at least partially soluble. The compositions according to the present invention are characterized by their outstanding stability, compared with formulations which do not contain these stabilizers.

11 Claims, No Drawings

STABILIZED ANTIMICROBIAL COMPOSITIONS

This is a continuation-in-part of application Ser. No. 07/054,217, filed May 26, 1987, now abandoned, which is a continuation of application Ser. No. 06/713,783, filed Mar. 20, 1985, now abandoned, which is a continuation-in-part of application Ser. No. 06/551,415, filed Nov. 14, 1983, now abandoned.

The present invention relates to stabilized antimicrobial compositions. More particularly, the invention relates to stabilized antimicrobial compositions containing halogenated cyanoacetamide as active ingredient.

The use of halocyanoacetamide in various compositions as an antimicrobial agent is well known for various applications as described in U.S. Pat. No. 2,419,888; U.S. Pat. No. 3,493,658 and Belgian Patent No. 668,336. Certain of the compounds are useful as slimicides in aqueous systems such as paper pulp and others are useful in the finishing of textiles.

In the preparation, storage, shipment and use of antimicrobial agents it is often desirable to employ the agents in the form of liquid concentrate compositions. Such compositions should be stable over extended periods under a variety of conditions of temperature, humidity, freeze-thaw cycles and the like, should be compatible with conventional container materials (glass, plastics etc.) and readily dilutable in the formulation of treating compositions. It would be most desirable to provide a stable liquid concentrate composition containing a halocyanoacetamide as active ingredient.

In some cases, particularly when water is also present in the formulations of the antimicrobial halocyanoacetamide compound in some organic solvents, it has been reported that the decomposition of the antimicrobial halogenated amide is accelerated. In order to reduce the adverse impact of water upon said compositions, there are disclosed various classes of stabilizers such as aldehydes (U.S. Pat. No. 4,163,798), sulfamoyl compounds (U.S. Pat. No. 4,163,797), cyclic ethers (U.S. Pat. No. 4,190,668), quaternary ammonium or phosphonium compounds (U.S. Pat. No. 4,163,796) or some azine compounds (U.S. Pat. No. 4,163,795), used in concentrations of 0.5% to 5% by weight of the formulation.

In our previous Israeli Patent Nos. 65126, 65290 and 65419, several distinct groups of organic solvents: propylene glycols, cellosolves and organic esters of phosphoric acid, respectively, were disclosed, being found to be quite suitable in formulations containing dibromonitrilopropionamide. Said formulations were found to be quite stable retaining high active ingredient concentrations and accordingly high antimicrobial activity for long periods of time.

Although the above formulations are characterized by a relatively long shelf life it was found that for more prolonged periods of time which include shipping and storage some decomposition is nevertheless encountered. Consequently, it is desirable to provide a means to substantially reduce the decomposition of even such formulations. Therefore it is an object of the present invention to provide stabilized halocyanoacetamide antimicrobial compositions. It is another object of the present invention to provide stabilized halocyanoacetamide antimicrobial compositions, using a stabilizer, without neutralizing their biocidal efficiency. Thus, the invention consists of stabilized antimicrobial compositions, comprising a solution of an antimicrobial amount of 2,2-dibromo-3-nitrilopropionamide in water miscible organic solvents in which 2,2-dibromo-3-nitrilopropionamide is at least partially soluble, selected from the group consisting of di-, tri- and polyalkylene glycols of ethylene and propylene, or a mono- or di- lower alkyl or phenyl ether, or ester thereof, propylene glycol and Cellosolve compounds and any mixture thereof, wherein the composition comprises a stabilizing amount of at least one chain breaking antioxidant of the phenolic or amine type in the range of from 0.001% to 0.5% by weight of the total composition. The term "stabilizing amount" as employed herein refers to an amount of stabilizer sufficient to measurably reduce the decomposition rate of the halocyanoacetamide reagent in the antimicrobial composition.

The crux of the present invention is based on the chance discovery that chain breaking antioxidants of the phenolic and amine type are effective in stabilizing the above 2,2-dibromo-3-nitrilopropionamide (known as DBNPA) formulations. This lead the inventors to a thorough investigation of the decomposition mechanism of solutions of DBNPA in which it was found that the decomposition proceeds by other means than those previously known. Thus, as had been reported previously, hydrolysis, which proceeds by an ionic pathway, is one route of decomposition, and reaction with nucleophiles is another. It now appears from the study of the inventors that very serious DBNPA chain decomposition is induced in its formulations by systems which produce free radicals. Free radical degradation can be induced by one or more factors such as air, heat or metallic contaminants.

The exact details of the halocyanoacetamide radical chain decomposition is not yet fully elucidated, but it seems to be similar in character to that frequently used to describe free radical oxidation:

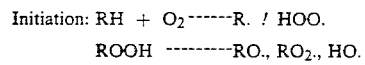
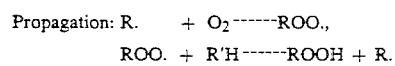

The initiation step in such chemical processes are known to be induced by light, heat or ionizing radiation. Hydroperoxide contaminants in the system can be decomposed to initiate the chain reaction under the influence of metallic impurities. Therefore, four different classes of anti-oxidants or radical inhibitors have been defined, based on the means by which they interfere with the oxidation reaction: peroxide scavengers, metal deactivators, light absorbers and chain (reaction) breakers. Inhibitors may themselves be consumed in the process, and one can conceivably add reagents to the system which function as inhibitor regenerators, which group of antioxidants may be added as a fifth sub-class.

It has been found that of the four basic classes of radical inhibitors, as defined in H. Mark's Encyc. of Polymer Science & Technology, Vol. 2, pages 173–178 (1965) or by G. Scott, Chem. & Ind. Feb. 16th, 1963 (pages 271–278), only the chain breaking antioxidants are effective stabilizers for halocyanoacetamide formulations against decomposition of this type. However, the manner in which these compounds serve to stabilize DBNPA is not entirely clear. Since the latter is an oxidizing agent and is present in overwhelming concentrations with respect to the stabilizers as used in the invention, it would have been expected that they would be rapidly neutralized, thereby losing their stabilizing power. That this is not the case is indeed surprising.

In the prior patents disclosing various stabilizers for such formulations, no explanation is given of the mechanism involved. However, they are basically different from the stabilizers according to the present invention both in their nature and even as regards the amounts of stabilizers suggested to be utilized. Whereas according to the prior patents, the preferred amounts of stabilizers are in the range of between 0.5% to 5% by weight of the total components, according to the present invention these amounts are in the range of between 0.001% to 0.5% which indicates a different mechanism for the stabilizer.

The halocyanoacetamide antimicrobial agents employed in the practice of this invention are alpha-haloamides and preferably halogenated nitrilopropionamides. Examples of such compounds are: 2-bromo-3-nitrilopropionamide, 2-bromo-2,3-dinitrilopropionamide, 2,2-dibromo-3-nitrilopropionamide, 2-chloro-2-bromo-2,3-dinitrilopropionamide and the like. Of particular interest are the dibrominated nitrilopropionamides such as: N-(n-butyl-2,2-dibromo-3-nitrilopropionamide, 2,2-dibromo-3-nitrilopropionamide and the like. In particular the latter compound (DBNPA) is most suitable and commercially available. Although in the specification and in the tests of the antimicrobial formulations DBNPA was utilized as active ingredient it should be understood that other halocyanoacetamides are included in the scope of the present invention their behaviour being the same as that of DBNPA. The ultimate concentration of the halocyanoacetamide as the active ingredient in the composition is in the range of 0.5 to 500 parts per million.

The contrast between the behaviour of and the purpose called upon to be served by the stabilizers of the invention on the one hand, and antioxidants commonly used in industry, on the other, can be seen in the following discussion. The latter are used to protect polymers, petroleum products and food from attack by an oxidizing agent. They are effective in very low concentrations because the species they are called upon to neutralize are themselves present in the system in very low concentrations, as low as parts per million or even less.

Thus, for example, they may be required to complex a trace metal which may be present as a deleterious contaminant in the system. Or they may react with peroxides or free radicals produced in minute concentrations by the oxidant or otherwise. The antioxidant is thus present in concentrations orders of magnitude greater than that of the oxidizing agent.

However, the system in the present invention is not a parallel situation. The object at the outset was to endeavor to stabilize an active halogen compound, intended for use as an antimicrobial agent, against premature decomposition in its formulated solutions. Its concentration in these solutions is of the order of tens of percents and not in parts per million. Such stabilization could not be at the expense of neutralizing the oxidative power of the reagent, lest its effectiveness as an antimicrobial be lost. By the use of the stabilizers defined in the present application, decomposition is remarkably reduced, even though in this case it is the oxidizing agent which is present in concentrations orders of magnitude greater than that of the antioxidant. Though stabilized, surprisingly the reagent retains its oxidizing ability. This is shown by the iodometric test described in the specification and by the fact that these solutions indeed remain antimicrobial as shown in the Examples. It is furthermore surprising that those materials which were found to be effective as stabilizers are not themselves destroyed by the overwhelming concentration of oxidizing agent present in the system. It has been shown by published studies that extremely few organic materials are inert vis-a-vis the halocyanoacetamides.

The discovery that low concentrations of chain breaking antioxidants (CBAs) can stabilize certain solutions of halocyanoacetamides was not a deduction based upon systems known to be of comparable chemical behaviour. CBAs are thought to be effective by interfering with the Propagation Step (in a mechanism such as that shown on page 5 of the Specification), in those cases in which the Propagation Step represents many repeating transformations produced by regenerated free radicals, i.e. when the radical chain reaction is long. Prior to the Applicants' work on these antimicrobial systems, there was no report of their decomposition proceeding by a free-radical chain reaction. It can only be assumed that this is the case since the discovery that CBAs influence the stability of these solutions was made empirically. This is the only existing evidence that a free radical chain decomposition reaction is involved.

The phenolic and amine type chain breaking antioxidants found to be useful according to the present invention can be represented by the following comprehensive formula:

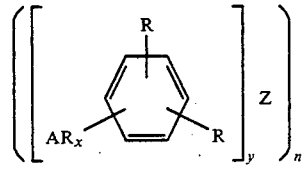

R=H, straight chain, branched or cyclic alkyl, alkaryl or aryl radical, being the same or different when there is more than one;
A=oxygen or nitrogen;
Z=R, AR$_x$, alkoxy methylene, methylene or alkylidene radical, and
n, x, y=1 or 2.

Typical examples of these stabilizers are enumerated hereafter:

PHENOLIC TYPE CHAIN BREAKING ANTIOXIDANTS

| | Trade name | Supplier |
|---|---|---|
| Butylated hydroxytoluene | Tenox BHT | Eastman |
| 2,6-di-tert butyl-p-cresol | Tenamene 3 | Eastman |
| 2,6-di-tert butyl-p-cresol | Topanol 0 | ICI |
| o and p-phenylphenol | Parazone | |
| 2,2'-methylene bis(4-methyl-6-tert-butyl phenol) | A.O. 2246 | American Cyanamid |
| 4,4'-methylene bis(6-tert-butyl-o-cresol) | A.O. 720 | Ethyl Corp |
| 4,4'-butylidene bis(6-tert-butyl-m-cresol) | Santowhite | Monsanto |
| 2,2-methylene bis(4-methyl-6 nonyl-phenol) | Naugawhite | Naugatuck Chem. |
| Mono-tert-butyl hydroquinone | MTBHQ | Eastman |
| 4,4'-bis(2,6-ditert butylphenol) | EA 712 | Ethyl Corp |
| 2,6-di-tert-butyl-α-methoxy-p-cresol | EA 762 | Ethyl Corp |

AMINE TYPE CHAIN BREAKING ANTIOXIDANTS

|  | Trade Name | Supplier |
|---|---|---|
| N-cyclohexyl-N'-phenyl-p-phenyl-enediamine | Santoflex | Monsanto |
| p,p'-diaminodiphenylmethane | Tonox | Naugatuck Chem. |
| N,N'-diphenylethylenediamine | Stabilite | C.P.Hall |
| N,N'-di-β-naphthyl-phenylenediamine | Nonox C.I. | ICI |
| N-phenyl-β-naphthylamine | PBN | Monsanto |
| 4,4'-dimethoxydiphenylamine | Thermoflex | |

All these stabilizers are commercially available and therefore easily obtainable. In particular the following compounds were found to be suitable and to give outstanding stability to formulations containing DBNPA: 2,6-di-tert-butyl-p-cresol (Topanol 0), 4,4'-bis(2,6-ditert-butylphenol)-(EA 712), 2,6-di-tert-butyl-α-methoxy-p-cresol (EA 762) and N-phenyl-β-naphthylamine.

Having discovered that the phenol and amine type antioxidants of the invention are effective in stabilizing DBNPA formulations, it may have been thought that this is a common property of the antioxidants used extensively in the rubber, plastics and food industries to stabilize organic compounds against oxidative deterioration. However not all antioxidants were found to be effective in the present invention. Thus for instance, antioxidants known as preventive antioxidants selected from ultraviolet absorbers, peroxide and hydroperoxide decomposers, or metal complexants do not have a stabilizing influence on compositions of antimicrobial aqueous solutions containing DBNPA. Table 1 illustrates in a clear manner the poor results obtained in attempts to stabilize such compositions when antioxidants such as ascorbic acid, known as a metal complexant, or trimethyl phosphite, known as a hydroperoxide decomposer, were utilized in antimicrobial formulations containing 20 parts DBNPA, 60 parts dipropylene glycol and 20 parts H$_2$O (all parts are by wt.).

on DBNPA formulations was a fortunate chance discovery.

Table 1 as well as others presented in the specification, contains data collected at ambient temperature under conditions deliberately accelerated to facilitate decompositions. This was achieved by storing relatively small samples of the test formulations in large transparent or translucent bottles thereby exposing the materials to considerable volumes of oxygen contained in the air of the head space. In addition, the bottles were placed near 40 W fluorescent lamps. Such tests are designated as accelerated decomposition tests in the Tables where appropriate.

The rate of decomposition of the DBNPA was determined by measuring the relative DBNPA content of the various antimicrobial compositions using an iodometric test. In this iodometric test, an excess of KI is added to the antimicrobial composition and the amount of elemental iodine which has been liberated from the potassium iodide—by the oxidation of KI with the DBNPA—is determined by titration with a standard solution of sodium thiosulfate. The amount of DBNPA present in the composition tested, is subsequently calculated on the basis of the amount of elemental iodine liberated thereby.

The results of Tables 1 and 24 show that these antioxidants (the metal complexant and the hydrogen peroxide decomposer) do not have any practical influence on the decomposition of DBNPA in the aqueous formulations. As already mentioned, t-butyl-thiocresol actually accelerates DBNPA decomposition.

As stated at the outset, other classes of stabilizers for DBNPA have been used in concentrations of 0.5% to 5%. Although the specifications in the cited patents make reference to lower amounts, no actual examples of stabilization with lower amounts are presented therein.

The actual mechanism by which the stabilizers of the invention act, as said, has not been fully elucidated. However, the stabilizers which are employed are clearly not active as antioxidants of the oxidizing activ-

TABLE 1

Accelerated decomposition tests of DBNPA in dipropylene glycol at ambient temperature.

| Without stabilizer | | | With 0.1% trimethyl phosphite | | | With 0.1% ascorbic acid | | |
|---|---|---|---|---|---|---|---|---|
| Time (days) | DBNPA (% w/w) | Decomposition (%) | Time (days) | DBNPA (% w/w) | Decomposition (%) | Time (days) | DBNPA (% w/w) | Decomposition (%) |
| 0 | 19.4 | 0 | 0 | 19.0 | 0 | 0 | 19.4 | 0 |
| 18 | 18.9 | 2.6 | 18 | 18.2 | 4.2 | 17 | 18.3 | 5.7 |
| 33 | 18.2 | 6.2 | 33 | 17.6 | 7.4 | 32 | 17.8 | 8.2 |
| 47 | 17.7 | 8.8 | | | | 46 | 17.4 | 10.3 |
| 75 | 16.7 | 13.9 | 78 | 15.7 | 17.4 | 74 | 16.1 | 17.0 |

Neither is ascorbic acid effective in stabilizing DBNPA in its formulations in ethyl Cellosolve (cf. Table 24). A still further example of contrast with the prior art is shown in Table 23 which shows the effect of t-butylthiocresol on a DBNPA formulation. Thiophenols are know to be oxidation inhibitors and have been considered in the same vein as 2,6-di-tert-butyl-p-cresol for application in oxidation inhibition (cf. CA 63, 1359d [1965]). However, though the latter compound is an effective stabilizer for DBNPA formulations, the thiophenol can be seen in Table 23 to be a destabilizing additive. The remarkable positive stabilizing effect of the phenol and amine type antioxidants of this invention ity of DBNPA, since the small amounts present in the composition are not such as to effectively counterbalance the large amount of oxidizing materials present, i.e. DBNPA and certain of its decomposition products.

It will therefore be understood by the skilled person that these stabilizers are termed "chain-breaking antioxidants" in the specification only in as much as they are so known as a class, and for ease and simplicity of reference, and this term does not necessarily imply the function of the stabilizing DBNPA.

It should be noted that the prior art teaches away from the use of antioxidants for stabilizing DBNPA. For instance, Burk et al., U.S. Pat. No. 4,163,798 teaches (col. 10, lines 7-11) that DBNPA is rendered non-oxidizing in an extent equal to that amount of the compound which has decomposed. The KI reagent, used in the test method, is also destroyed in an equivalent amount. Thus, the skilled chemist would have avoided, on the basis of the teachings of Burk et al., the use of any antioxidant compound, which might decompose DBNPA and so render it unfit for use as an antimicrobial agent. On the other hand, the antioxidant compound itself would be expected to be equally decomposed and rendered ineffective thereby. In the light of this patent, therefore, the ability of using the stabilizers of the invention is even more surprising.

Furthermore, an attempt to destroy DBNPA by using a compound which neutralizes its oxidizing activity, if desired for any reason, should of course be carried out with an excess of such neutralizing material. This is also taught by Burk et al. (col. 9, lines 62-67), which specifies that excess of KI is employed to achieve the complete decomposition of DBNPA to inactive species, although this of course is only a test procedure which in fact does destroy the DBNPA, and which, as will be appreciated by any chemist, can be used only for analytical purposes. This fact is further evidence that the less than 1% antioxidant used according to the invention has no appreciable effect on the said oxidizing activity of DBNPA.

Organic solvents which are suitable in the antimicrobial formulations containing DBNPA, include water miscible organic solvents in which the halocyanoacetamide compound is at least partially soluble. Preferably the organic solvent is a single compound or mixture of solvents in which the halocyanoacetamide is soluble at normal room temperature (i.e. from about 20° to 30° C.) to the extent of at least 5 parts by weight of the compound in about 95 parts by weight of the solvent. The most preferred water miscible organic solvents are those in which the antimicrobial compound is soluble to the extent of at least about 10 parts by weight of the compound in about 80 parts by weight of the solvent at normal room temperature. There are indeed numerous organic solvents useful, possessing the above properties such as: polyalkylene glycol or an ether thereof including: triethylene glycol, polyethylene glycol, propylene glycols, such as mono- di- and polypropylene glycols, tetraethylene glycol, diethylene glycol and its mono- and di-lower alkyl (i.e. $C_1$ to $C_6$) and phenyl ethers and esters thereof, Cellosolves and esters of phosphoric acids. The amount of the aforementioned water miscible organic solvents employed in the practice of the invention is not particularly critical. Advantageously, however a sufficient amount is employed to prevent precipitation of the halocyanoacetamide during shipping, storage and use of the aqueous antimicrobial composition. The preferred amount of the organic solvent desirably employed will thus depend upon various factors such as the solubility of the halocyanoacetamide in the organic solvent, the desired concentration of the halocyanoacetamide in the composition and the like. However as a general rule the organic solvent constitutes from about 5 to about 90, preferably from about 25 to about 75 and most preferably from about 35 to about 70 percent by weight of the total antimicrobial composition.

The amount of water contained in the aqueous antimicrobial compositions according to the present invention is not particularly critical to the practice of the invention. However as a general rule the compositions according to the present invention employ water in an amount of from 5 to about 90 and preferably from about 15 to about 70 and most preferably from about 20 to about 60 weight per cent based upon the weight of the total antimicrobial composition.

The order of combination of the above described ingredients is not critical to obtain formulations of a decreased decomposition rate relative to that obtained with the corresponding non-stabilized compositions. However, in order to avoid excessive amounts of decomposition prior to stabilization, it is generally desirable to avoid prolonged exposure of the antimicrobial compound in the composition, prior to addition of the stabilizer according to the present invention. Similarly, it is generally desirable, in order to retain optimum antimicrobial activity, to prepare, store, transport and handle the stabilized compositions of the invention at the lowest practical temperature, normally being the ambient temperature.

The stabilized antimicrobial compositions of the present invention preferably contain the following weight ratios of components: halocyanoacetamide from 1% to its solubility limit, water from 0 to 40% and the balance (to make the total of 100%, except for the stabilizer) the organic solvent or solvents and 0.001% to 0.5% of said stabilizer.

Hereafter will be summarized some of the results concerning the stability of antimicrobial compositions containing DBNPA, expressed as the rate of DBNPA decomposition, in the presence of 0.1% by weight of stabilizer according to the present invention and without it, using various organic solvents.

The antimicrobial compositions Rate of decomposition

| (% w/w) | | | $K_1$ (%/day) | | |
|---|---|---|---|---|---|
| DBNPA | $H_2O$ | Organic solvent | No additive | EA 712 | Topanol 0 |
| 20 | 20 | PEG 200 | 0.06 | 0.04 | 0.008 |
| 20 | 20 | DPG | 0.06 | n.d. | 0.010 |
| 20 | 20 | DEG | 0.05 | 0.013 | 0.013 |
| 20 | 20 | DEG Me | 0.04 | 0.009 | 0.009 |
| 30 | 20 | DEG Me | 0.09 | n.d. | 0.040 |
| 20 | 20 | Cellosolve | 0.04 | 0.004 | 0.004 |
| 30 | 20 | Cellosolve | 0.14 | n.d. | 0.015 |

(n.d. = not determined; DEG Me = diethyleneglycol monomethyl ether; Cellosolve = 2-Ethoxy-ethanol; PEG 200 = polyethylene glycol 200; DPG = dipropylene glycol; DEG = diethylene glycol).

The above results show that in most cases the stability in the presence of a chain breaking antioxidant (E.A. 712 or Topanol 0) increased almost ten times compared with the compositions which do not possess the stabilizer.

In the following Table 2 are presented the results concerning the stability of DBNPA in aqueous solutions of PEG 200 (polyethyleneglycol, M.W. 200) at ambient temperature carried out in the presence of 2,6-di-tert-butyl-p-cresol also known as Topanol 0, a commercial antioxidant. The test was carried out in polyethylene containers, the solutions consisting of 20% DBNPA, 20% $H_2O$ and 60% PEG-200 and 0.1% (all concentrations being in wt. per cent) of Topanol 0. For comparison purposes, the results obtained in the absence of the stabilizer are also presented.

TABLE 2

Decomposition tests of DBNPA in PEG 200 at ambient temperature.

| Without stabilizer | | | With 0.1% of Topanol 0 | | |
|---|---|---|---|---|---|
| Time (days) | DBNPA (% w/w) | Decomposition (%) | Time (days) | DBNPA (% w/w) | Decomposition (%) |
| 0 | 20.0 | 0 | 0 | 20.0 | 0 |
| 33 | 19.5 | 2.5 | 32 | 20.0 | 0 |
| 64 | 19.2 | 4.0 | 63 | 19.9 | 0.5 |
| 96 | 18.9 | 5.6 | 95 | 19.8 | 1.0 |
| 160 | 18.1 | 9.5 | 159 | 19.8 | 1.0 |
| | | | 214 | 19.4 | 3.0 |

The above results clearly show the beneficial effect which is imparted by 0.1% of Topanol 0 to the stability of the formulations containing DBNPA in PEG 200. These results are completely satisfactory compared with the rates of decomposition which are encountered when previously known stabilizers are utilized.

In the following Table 3 are presented the results obtained with aqueous solutions of DPG (dipropylene glycol) at ambient temperature in polyethylene containers. The solutions consisted of 20% DBNPA, 20% H₂O and 60% DPG and 0.1% of Topanol 0. For comparison purposes, the results obtained in the absence of the stabilizer are also presented.

TABLE 3

Decomposition tests of DBNPA in DPG at ambient temperature.

| Without stabilizer | | | With 0.1% of Topanol 0 | | |
|---|---|---|---|---|---|
| Time (days) | DBNPA (% w/w) | Decomposition (%) | Time (days) | DBNPA (% w/w) | Decomposition (%) |
| 0 | 19.1 | 0 | 0 | 18.9 | 0 |
| 59 | 17.7 | 7.3 | 59 | 18.8 | 0.5 |
| 91 | 16.7 | 12.6 | 91 | 18.7 | 1.1 |
| | | | 133 | 18.7 | 1.1 |
| | | | 229 | 18.5 | 2.1 |

The beneficial effect of the small amount of Topanol 0 on the stability of DBNPA in aqueous dipropylene glycol appears clearly from the above results.

In the following Table 4 are presented the results obtained with aqueous solutions of DEG (diethylene glycol) at ambient temperature in polyethylene containers. The solutions consisted of 20% DBNPA, 20% H₂O and 60% DEG and 0.1% of E.A. 712 and Topanol 0, respectively. For comparison purposes, the results obtained in the absence of stabilizers are also presented:

TABLE 4

Decomposition tests of DBNPA in DEG at ambient temperature.

| Without stabilizer | | | With 0.1% of E.A. 712 | | | With 0.1% of Topanol 0 | | |
|---|---|---|---|---|---|---|---|---|
| Time (days) | DBNPA (% w/w) | Decomposition (%) | Time (days) | DBNPA (% w/w) | Decomposition (%) | Time (days) | DBNPA (% w/w) | Decomposition (%) |
| 0 | 20.0 | 0 | 0 | 19.9 | 0 | 0 | 20.0 | 0 |
| 33 | 19.6 | 2.0 | 32 | 19.9 | 0 | 32 | 19.8 | 1.0 |
| 64 | 19.3 | 3.5 | 63 | 19.8 | 0.5 | 63 | 19.8 | 1.0 |
| 96 | 19.2 | 4.0 | 95 | 19.7 | 1.0 | 95 | 19.8 | 1.0 |
| 163 | 18.5 | 7.5 | 162 | 19.4 | 2.5 | 162 | 19.7 | 1.5 |
| | | | 214 | 19.2 | 3.5 | 214 | 19.6 | 2.0 |

In the following Tables 5 and 6 are presented the results of decomposition tests obtained with aqueous solutions of DEG Me (diethylene glycol monomethyl ether) at ambient temperature tested in polyethylene containers. In Table 5 the solution composition was 20% DBNPA, 20% H₂O and 60% DEG Me and 0.1% of E.A. 712 and 0.1% Topanol 0 respectively as stabilizers, while in Table 6 the solution composition was 30% DBNPA, 20% H₂O and 50% DEG Me. For comparison purposes, the results obtained in the absence of any stabilizer are also presented.

TABLE 5

Decomposition tests of DBNPA in DEG Me at ambient temperature.

| Without stabilizer | | | With 0.1% of E.A. 712 | | | With 0.1% of Topanol 0 | | |
|---|---|---|---|---|---|---|---|---|
| Time (days) | DBNPA (% w/w) | Decomposition (%) | Time (days) | DBNPA (% w/w) | Decomposition (%) | Time (days) | DBNPA (% w/w) | Decomposition (%) |
| 0 | 20.1 | 0 | 0 | 20.1 | 0 | 0 | 20.1 | 0 |
| 33 | 19.8 | 1.5 | 32 | 20.0 | 0.5 | 32 | 20.1 | 0 |
| 64 | 19.6 | 2.5 | 63 | 19.9 | 1.0 | 63 | 20.1 | 0 |
| 96 | 19.2 | 4.5 | 95 | 19.9 | 1.0 | 93 | 20.0 | 0.5 |
| 161 | 18.5 | 8.0 | 160 | 19.6 | 2.5 | 160 | 19.6 | 2.5 |
| | | | 214 | 19.2 | 4.5 | 214 | 19.4 | 3.5 |

TABLE 6

Decomposition tests of DBNPA in DEG Me at ambient temperature.

| Without stabilizer | | | With 0.1% of Topanol 0 | | |
|---|---|---|---|---|---|
| Time (days) | DBNPA (% w/w) | Decomposition (%) | Time (days) | DBNPA (% w/w) | Decomposition (%) |
| 0 | 30.0 | 0 | 0 | 30.0 | 0 |
| 53 | 28.2 | 6.0 | 53 | 29.4 | 2.0 |
| 87 | 27.4 | 8.7 | 87 | 29.0 | 3.3 |
| 130 | 26.6 | 11.3 | 130 | 28.7 | 4.3 |
| | | | 261 | 28.2 | 6.0 |

In the following Tables 7 and 8 are presented the results of decomposition tests obtained with aqueous solutions of Cellosolve in polyethylene containers at ambient temperature. As shown in our previous Israeli Patent No. 65290, monoethers of ethylene glycol, commonly encountered under the name Cellosolves are useful in formulations with DBNPA. In Table 7, the solution composition was 20% DBNPA, 20% H₂O and 60% Ethyl Cellosolve (CELL), which is 2-ethoxyethanol and 0.1% E.A. 712 and 0.1% Topanol 0 respectively as stabilizers, while in Table 8 the solution composition was 30% DBNPA, 20% H₂O and 50% CELL in the presence of 0.1% of Topanol 0 as stabilizer. For comparison purposes, the results obtained in the absence of any stabilizer are also presented.

(w/w) as appears from the results given in the following Tables 11 and 12.

TABLE 7

Decomposition tests of DBNPA in CELL at ambient temperature.

| Without stabilizer | | | With 0.1% of E.A. 712 | | | With 0.1% of Topanol 0 | | |
|---|---|---|---|---|---|---|---|---|
| Time (days) | DBNPA (% w/w) | Decomposition (%) | Time (days) | DBNPA (% w/w) | Decomposition (%) | Time (days) | DBNPA (% w/w) | Decomposition (%) |
| 0 | 20.0 | 0 | 0 | 19.9 | 0 | 0 | 19.9 | 0 |
| 33 | 19.6 | 2.0 | 32 | 19.9 | 0 | 32 | 19.9 | 0 |
| 64 | 19.5 | 2.5 | 63 | 19.9 | 0.5 | 63 | 19.9 | 0 |
| 96 | 19.3 | 3.5 | 95 | 19.8 | 0.5 | 95 | 19.9 | 0 |
| 162 | 18.6 | 7.0 | 161 | 19.8 | 0.5 | 161 | 19.8 | 0.5 |
| | | | 214 | 19.8 | 0.5 | 214 | 19.7 | 1.0 |

TABLE 8

Decomposition tests of DBNPA in Cellosolve at ambient temperature.

| Without stabilizer | | | With 0.1% of Topanol 0. | | |
|---|---|---|---|---|---|
| Time (days) | DBNPA (% w/w) | Decomposition (%) | Time (days) | DBNPA (% w/w) | Decomposition (%) |
| 0 | 29.6 | 0 | 0 | 29.6 | 0 |
| 53 | 27.5 | 7.1 | 53 | 29.3 | 1.0 |
| 88 | 26.0 | 12.2 | 88 | 29.3 | 1.0 |
| | | | 130 | 29.0 | 2.0 |
| | | | 229 | 28.5 | 3.7 |

The beneficial effect of these stabilizers on DBNPA in the formulations with a water miscible organic solvent, was found to be present also in dilute solutions of DBNPA. Tables 9 and 10 summarize the results concerning the stability of 5% DBNPA, 75% propylene glycol (PG) and 20% H₂O, and 10% DBNPA, 70% PG and 20% H₂O respectively.

TABLE 9

Accelerated decomposition tests of dilute solution of DBNPA in propylene glycol at ambient temperature.

| Without stabilizer | | | With 0.1% of E.A. 712 | | |
|---|---|---|---|---|---|
| Time (days) | DBNPA (% w/w) | Decomposition (%) | Time (days) | DBNPA (% w/w) | Decomposition (%) |
| 0 | 4.9 | 0 | 0 | 4.9 | 0 |
| 15 | 4.8 | 2.0 | 15 | 4.9 | 0 |
| 44 | 4.0 | 18.4 | 44 | 4.7 | 4.1 |
| | | | 60 | 4.4 | 10.2 |

TABLE 10

Accelerated decomposition tests of dilute solutions of DBNPA in propylene glycol at ambient temperature.

| Without stabilizer | | | With 0.1% of E.A. 712 | | |
|---|---|---|---|---|---|
| Time (days) | DBNPA (% w/w) | Decomposition (%) | Time (days) | DBNPA (% w/w) | Decomposition (%) |
| 0 | 9.6 | 0 | 0 | 9.6 | 0 |
| 15 | 9.2 | 4.2 | 15 | 9.6 | 0 |
| 44 | 8.8 | 8.3 | 44 | 9.3 | 3.1 |
| 60 | 7.6 | 20.8 | 60 | 9.2 | 4.2 |
| | | | 122 | 7.8 | 18.8 |

The above results clearly show that the stabilizers according to the present invention have a beneficial effect even in dilute solutions of DBNPA. The concentration of the stabilizer may be reduced below 0.1%

TABLE 11

Accelerated decomposition tests of DBNPA in dipropylene glycol (DPG) at ambient temperature. (Solution compositions 20% DBNPA - 20% H₂O - 60% DPG).

| Without stabilizer | | | With 0.015% of E.A. 712 | | |
|---|---|---|---|---|---|
| Time (days) | DBNPA (% w/w) | Decomposition (%) | Time (days) | DBNPA (% w/w) | Decomposition (%) |
| 0 | 19.9 | 0 | 0 | 19.9 | 0 |
| 17 | 19.4 | 2.5 | 17 | 19.8 | 0.5 |
| 30 | 19.0 | 4.5 | 30 | 19.4 | 2.5 |
| 43 | 18.4 | 7.5 | 43 | 19.0 | 4.5 |

As appears from Tables 12 and 13 below, similar results concerning the decomposition of DBNPA are obtained in accelerated tests, when either 0.1% or 0.05% w/w of N-phenyl-2-naphthylamine is added to the formulations.

TABLE 12

Accelerated decomposition of DBNPA in DPG at ambient temperature. (Solution composition: 20% DBNPA - 20% H₂O - 60% DPG).

| Without stabilizer | | | With 0.05% of N-phenyl-2-naphthylamine | | |
|---|---|---|---|---|---|
| Time (days) | DBNPA (% w/w) | Decomposition (%) | Time (days) | DBNPA (% w/w) | Decomposition (%) |
| 0 | 19.8 | 0 | 0 | 19.8 | 0 |
| 15 | 19.2 | 3.0 | 15 | 19.6 | 1.0 |
| 35 | 18.4 | 7.1 | 35 | 19.5 | 1.5 |
| 47 | 17.9 | 9.6 | 48 | 19.2 | 3.0 |

TABLE 13

Accelerated decomposition tests of DBNPA in DPG at ambient temperature. (Solution composition: 20% DBNPA - 20% H₂O - 60% DPG).

| Without stabilizer | | | With 0.1% of N-phenyl-2-naphthylamine | | |
|---|---|---|---|---|---|
| Time (days) | DBNPA (% w/w) | Decomposition (%) | Time (days) | DBNPA (% w/w) | Decomposition (%) |
| 0 | 19.4 | 0 | 0 | 19.4 | 0 |
| 18 | 18.9 | 2.6 | 17 | 19.0 | 2.1 |
| 33 | 18.2 | 6.2 | 32 | 18.9 | 2.6 |
| 47 | 17.7 | 8.8 | 74 | 18.5 | 4.6 |
| 75 | 16.7 | 13.9 | 104 | 18.0 | 7.2 |

In the following Table 14 are presented the results obtained in accelerated tests of DBNPA in DPG at ambient temperature using a solution of 0.005% of Topanol 0 as stabilizer.

TABLE 14

Accelerated decomposition tests of DBNPA in DPG at ambient temperature. (Solution composition: 20% DBNPA - 20% H₂O - 60% DPG).

| | Without stabilizer | | | With 0.005% Topanol O | |
|---|---|---|---|---|---|
| Time (days) | DBNPA (% w/w) | Decomposition (%) | Time (days) | DBNPA (% w/w) | Decomposition (%) |
| 0 | 19.3 | 0 | 0 | 19.3 | 0 |
| 21 | 18.7 | 3.1 | 21 | 19.0 | 1.6 |
| 33 | 18.2 | 5.7 | 33 | 18.7 | 3.1 |

It was found that even reducing the stabilizer concentration to as low as 0.001% resulted in improved stability of the above formulations.

Some experiments were performed with cellosolves as described in our prior Israeli Patent No. 65290. A formulation containing 20% DBNPA—20% H₂O and 60% of a mixture consisting of 7 parts of ethyl Cellosolve and 3 parts of hexyl Cellosolve, was exposed to an acelerated stability test at ambient temperature. An identical formulation containing in addition 0.01% Topanol 0 was tested under parallel conditions, whereby a significant improvement in stability was observed for the latter.

In the following Table 15 are summarized some results concerning the extent of decomposition of several formulations in various solvents, without additive and with 0.1% of Topanol 0. The tests were performed for a period of 20 months in containers kept at ambient temperature. The formulations consisted of: 20% DBNPA, 20% H₂O and 60% solvent, the specific organic solvent being different in each test.

TABLE 15

Influence of Topanol O (0.1% by wt.) on stability at ambient temperature of various formulations with different organic solvents.

| Solvent | Additive | Extent of decomposition |
|---|---|---|
| PEG 200 | None | 58% (after 20 months) |
| PEG 200 | 0.1% Topanol O | 11% (after 20 months) |
| Cellosolve | None | 61% (after 20 months) |
| Cellosolve | 0.1% Topanol O | 8% (after 20 months) |
| DEG monomethyl ether | None | 54% (after 20 months) |
| DEG monomethyl ether | 0.1% Topanol O | 9% (after 20 months) |
| DEG | None | 28% (after 20 months) |
| DEG | 0.1% Topanol O | 7% (after 20 months) |
| DPG | None | 9.4% (after 16 months) |
| DPG | 0.1% Topanol O | 5.4% (after 16 months) |

PEG = polyethylene glycol.
DEG = diethylene glycol.
DPG = dipropylene glycol.

In the following Tables 16 and 17, are summarized some results on accelerated decomposition tests of DBNPA in Dipropylene Glycol (DPG), at ambient temperature, without stabilizer and with 0.15% by weight of EA 762 (produced by Ethyl Corp)—in Table 16—and with 0.015% by wt. of EA 762 in Table 17.

TABLE 16

Accelerated Decomposition Tests of DBNPA in DPG at ambient Temperature. Solution composition: 20% DBNPA; 20% H₂O and 60% DPG

| | Without stabilizer | | | With 0.15% of E.A. 762 | |
|---|---|---|---|---|---|
| Time (days) | DBNPA (% w/w) | Decomposition (%) | Time (days) | DBNPA (% w/w) | Decomposition (%) |
| 0 | 19.9 | 0 | 0 | 20.1 | 0 |
| 17 | 19.4 | 2.5 | 17 | 20.0 | 0.5 |
| 30 | 19.0 | 4.5 | 30 | 19.6 | 2.5 |
| 43 | 18.4 | 7.5 | 43 | 19.2 | 4.5 |
| 56 | 18.0 | 9.5 | 56 | 18.9 | 6.0 |

TABLE 17

Accelerated Decomposition Tests of DBNPA in DPG at ambient Temperature. Solution composition: 20% DBNPA; 20% H₂O and 60% DPG

| | Without stabilizer | | | With 0.015% of EA 762 | |
|---|---|---|---|---|---|
| Time (days) | DBNPA (% w/w) | Decomposition (%) | Time (days) | DBNPA (% w/w) | Decomposition (%) |
| 0 | 19.9 | 0 | 0 | 19.9 | 0 |
| 17 | 19.4 | 2.5 | 17 | 19.8 | 0.5 |
| 30 | 19.0 | 4.5 | 30 | 19.4 | 2.5 |
| 43 | 18.4 | 7.5 | 43 | 19.0 | 4.5 |
| 56 | 18.0 | 9.5 | 56 | 18.7 | 6.0 |

As appears from the above Tables a beneficial effect is obtained even by incorporating the very small amount of 0.015% by wt. (Table 16) of a stabilizer according to the present invention, a ten fold increase in the amount of the same stabilizer (Table 17) imparts the same stability effect within this time frame.

In the following Tables 18 and 19 are summarized some results on accelerated decomposition tests in non-aqueous solutions, without stabilizer and with 0.1% of Topanol 0. The tests were carried out at ambient temperature using two different solvents: polyethylene glycol (PEG) 200 (in Table 18) and dipropylene glycol—DPG—(in Table 19).

TABLE 18

Accelerated Decomposition Tests of DBNPA in PEG 200 at ambient Temperature. Solution Composition: 20% DBNPA - 80% PEG 200.

| | Without Stabilizer | | | With 0.1% by wt. of Topanol O | |
|---|---|---|---|---|---|
| Time (days) | DBNPA (% w/w) | Decomposition (%) | Time (days) | DBNPA (% w/w) | Decomposition (%) |
| 0 | 19.3 | 0 | 0 | 19.3 | 0 |
| 12 | 18.8 | 2.6 | 12 | 19.2 | 0.5 |
| 26 | 18.7 | 3.1 | 26 | 19.0 | 1.0 |
| 40 | 18.7 | 3.1 | 40 | 19.0 | 1.6 |
| 56 | 18.7 | 3.1 | 56 | 19.0 | 1.6 |

TABLE 19

Accelerated Decomposition Tests of DBNPA in DPG at ambient Temperature. Solution Composition: 20% DBNPA - 80% DPG.

| | Without Stabilizer | | | With 0.1% by wt. of Topanol O | |
|---|---|---|---|---|---|
| Time (days) | DBNPA (% w/w) | Decomposition (%) | Time (days) | DBNPA (% w/w) | Decomposition (%) |
| 0 | 19.4 | 0 | 0 | 19.4 | 0 |
| 11 | 19.1 | 1.5 | 11 | 19.2 | 1.0 |
| 21 | 18.9 | 2.6 | 21 | 19.2 | 1.0 |
| 36 | 18.7 | 3.6 | 36 | 18.9 | 2.6 |

TABLE 19-continued

Accelerated Decomposition Tests of DBNPA in DPG at ambient Temperature. Solution Composition: 20% DBNPA - 80% DPG.

| Without Stabilizer | | | With 0.1% by wt. of Topanol O | | |
|---|---|---|---|---|---|
| Time (days) | DBNPA (% w/w) | Decomposition (%) | Time (days) | DBNPA (% w/w) | Decomposition (%) |
| 70 | 18.2 | 6.2 | 70 | 18.6 | 4.1 |

As appears from the above Tables 18 and 19 the stabilizers according to the present invention have the same beneficial effect stabilizing antimicrobial compositions in non-aqueous systems. Antimicrobial compositions in non-aqueous systems might be desirable for use in certain particular cases such as fuel additives.

In the following Tables 20 and 21 are summarized some results on accelerated decomposition tests with two different phenolic type stabilizers: AO 720 [4,4-methylene bis (b-tert-butyl-o-cresol)] and MTBHQ (mono-tert-butyl hydroquinone). The tests were carried out at ambient temperature using compositions consisting of 20% DBNPA —20% water and 60% propylene glycol.

TABLE 20

Accelerated decomposition tests of DBNPA in propylene glycol (stabilizer being AO 720).

| Without Stabilizer | | | With 0.1% by wt. of AO 720 | | |
|---|---|---|---|---|---|
| Time (days) | DBNPA (% w/w) | Decomposition (%) | Time (days) | DBNPA (% w/w) | Decomposition (%) |
| 0 | 19.9 | 0 | 0 | 19.9 | 0 |
| 15 | 19.5 | 2.0 | 15 | 19.8 | 0.5 |
| 31 | 19.0 | 4.7 | 31 | 19.5 | 2.0 |
| 50 | 18.0 | 9.5 | 50 | 19.0 | 4.5 |

TABLE 21

Accelerated decomposition tests of DBNPA in propylene glycol (stabilizer being MT BHQ).

| Without Stabilizer | | | With 0.1% by wt. of MTBHQ | | |
|---|---|---|---|---|---|
| Time (days) | DBNPA (% w/w) | Decomposition (%) | Time (days) | DBNPA (% w/w) | Decomposition (%) |
| 0 | 19.9 | 0 | 0 | 19.9 | 0 |
| 15 | 19.5 | 2.0 | 15 | 19.7 | 1.0 |
| 31 | 19.0 | 4.7 | 31 | 19.4 | 2.5 |
| 50 | 18.0 | 9.5 | 50 | 18.9 | 5.0 |

The above results clearly show the beneficial effect on the stabilizers according to the present invention.

In the following Table 22 are presented the rate of decomposition found with three different amine-type stabilizers, calculated from long range stability test at ambient temperature of DBNPA in aqueous dipropylene glycol (DPG) solutions.

TABLE 22

Long range stability tests of DBNPA in aqueous DPG solutions. Solution Composition: 20% DBNPA - 20% H$_2$O - 60% DPG. Rate of decomposition, K$_j$ (%/day)

| No additive | 0.1% by wt Nonox CI | 0.1% by wt Thermoflex | 0.1% by wt Santoflex |
|---|---|---|---|
| 0.06 | 0.015 | 0.018 | 0.023 | wherein:

Nonox CI—N,N'-di-p-naphthyl-p-phenylenediamine.
Thermoflex—4,4'-dimethoxydiphenylamine.
Santoflex—N-cyclohexyl-N'-phenyl-p-phenylenediamine.

The stabilizers for the antimicrobial compositions according to the present invention are selected from phenolic and amine type chain breaking antioxidants represented by the general formula given on page 11 of the specification. In the following Table 23 are given the results obtained with 4-t-butyl thiocresol, which is a known antioxidant, not included in the general formula of the stabilizers according to the present invention. The conclusion which can be drawn from the results given in Table 23 is that this antioxidant has an adverse influence on the stability of the antimicrobial compositions; in the presence of only 0.1% by weight of the additive, the decomposition rate of DBNPA is much higher than in its absence.

TABLE 23

Accelerated decomposition tests of DBNPA in DPG at ambient temperature with an antioxidant (not according to the present invention).

| Without Additive | | | With 0.1% 4-t-butyl thiocresol | | |
|---|---|---|---|---|---|
| Time (days) | DBNPA (% w/w) | Decomposition (%) | Time (days) | DBNPA (% w/w) | Decomposition (%) |
| 0 | 19.0 | 0 | 0 | 19.0 | 0 |
| 18 | 18.5 | 2.6 | 18 | 18.1 | 4.7 |
| 33 | 17.6 | 7.4 | 33 | 17.3 | 8.9 |
| 78 | 16.1 | 15.3 | 78 | 14.2 | 25.3 |

In the following Table 24, are given, also for comparison purposes, the results obtained with ascorbic acid, which is a known antioxidant, but not included in the general formula of the stabilizers according to the present invention.

TABLE 24

Decomposition of DBNPA in Cellosove at ambient temperature in the presence of ascorbic acid (an antioxidant not according to the present invention). Solution Composition: 20% DBNPA-20% water-60% Cellosove

| Without Additive | | | With 0.2% Ascorbic Ac. | | |
|---|---|---|---|---|---|
| Time (days) | DBNPA (% w/w) | Decomposition (%) | Time (days) | DBNPA (% w/w) | decomp. (%) |
| 0 | 20.0 | 0 | 0 | 20.0 | 0 |
| 34 | 19.7 | 1.5 | 30 | 19.5 | 2.5 |
| 49 | 19.6 | 2.0 | 50 | 19.2 | 4.0 |
| 82 | 19.4 | 3.0 | 80 | 18.9 | 5.5 |
| 110 | 19.2 | 4.0 | 90 | 18.8 | 6.0 |
| 140 | 19.0 | 5.0 | 110 | 18.6 | 7.0 |

As appears from the results obtained, the DBNPA antimicrobial composition decomposes at appreciable rates in the presence of ascorbic acid (a well-known antioxidant).

The presence of ascorbic acid even causes an increase in the decomposition rate of DBNPA.

The stabilized antimicrobial compositions according to the present invention are useful as slimicides in aqueous systems such as paper pulping processes and cooling towers and as sterilizing agents for dry-cleaning fluids. The compositions exhibit improved stability towards decomposition of the DBNPA antimicrobial active ingredient for extended periods of time under a wide variety of storage, packaging and handling conditions.

The microbiological activity of stabilized compositions according to the present invention was tested with liquors obtained from actual streams from the plant of a commercial paper mill. Microorganisms were isolated from such solutions and treated with 100 ppm of formulations of DBNPA in aqueous Ethyl Cellosolve (CELL) on the one hand, and DBNPA in aqueous dipropylene glycol, on the other. The formulations consisted of 20 parts DBNPA, 20 parts water and 60 parts of the organic solvent.

The following results were obtained:

|  | MO/ml, isolated from alkaline stream | |
|---|---|---|
|  | Init. soln. | After 3 hr. |
| CELL Formulation, without added stabilizer, | $4.5 \times 10^5$ | <10 |
| stabilized with 0.1% EA 712 | $4.5 \times 10^5$ | <10 |
| DPG Formulation, without added stabilizer, | $2.5 \times 10^6$ | <10 |
| stabilized with 0.1% EA 762 | $2.2 \times 10^6$ | <10 |
| stabilized with 0.1% Nonox CI | $2.5 \times 10^6$ | <10 |

It is seen from these data that the stabilizers did not diminish the activity of the biocide.

Summing up, as appears from the results presented in the Tables, the presence of the stabilizers according to the present invention reduces the amount of antimicrobial compound which decomposes by about 30 to 80%. Such decomposition reduction is of course relative to that which occurs under the same conditions in the absence of the chain breaking antioxidants of the phenolic or amine type. In general terms, the amount of stabilizer needed to achieve the desired degree of stabilization can vary depending upon the remainder of the composition (i.e. the identity and concentration of the other ingredients in the particular composition involved) and upon the particular stabilizer employed. The stabilizing amount within the meaning defined hereinbefore, will be generally in a broad range of 0.001% to 0.5% by weight of the total composition.

Of course, the smaller the amount of the antioxidant used, the lower the cost of the formulation. An optimum concentration will be sought to minimize cost yet achieve the required level of stability of the formulation. Methods for determining this optimum concentration are well known to persons skilled in the art.

In addition to the hereinbefore defined ingredients, the antimicrobial compositions according to the present invention can optionally contain other known ingredients used in the art for such compositions such as corrosion inhibitors, etc. Such optional ingredients can be inert in the sense that they neither inhibit nor accelerate decomposition of the antimicrobial compound. Alternatively, such optional ingredients can themselves be also used as co-stabilizers with DBNPA antimicrobial compositions.

For the sake of good order it is mentioned that in all the Tables given in this specification the percentages are by weight, unless otherwise stated.

While the invention has been described with specific embodiments thereof, it will be understood that it is capable of further modifications, and this patent is intended to cover any variation, uses or adaptations of the invention and including such departures from the patent disclosure as come within known or customary practice in the art to which the invention pertains and as may be applied to the essential features hereinbefore set forth and as fall within the scope of the invention.

We claim:

1. A stabilized antimicrobial composition, comprising a solution of an antimicrobial amount of from about 5 to about 30 percent of 2,2-dibromo-3-nitrilopropionamide in water miscible organic solvents in which 2,2-dibromo-3-nitrilo-propionamide is at least partially soluble selected from the group consisting of di-, tri- and polyalkylene glycols of ethylene and propylene, or a mono- or di- lower alkyl or phenyl ether, or ester thereof, propylene glycol and Cellosolve compounds and any mixture thereof, wherein the composition comprises a stabilizing amount of at least one chain breaking anti-oxidant of the phenolic or amine type in the range of from 0.005 to 0.2% by weight of the total composition, wherein said phenolic or amine type chain breaking antioxidant is represented by the formula:

$$\left\{ \left[ \begin{array}{c} R \\ \bigotimes \\ AR_x \quad R \end{array} \right]_y Z \right\}_n$$

wherein:
R=H, straight chain, branched or cyclic alkyl, phenylalkyl or phenyl radical, being the same or different when there is more than one wherein said alkyl is a $C_1$ to $C_9$ alkyl;
A=oxygen or nitrogen;
Z=R, $AR_x$, alkoxy methylene, methylene or alkylidene radical; and
n, x, y=1 or 2.

2. The stabilized antimicrobial composition according to claim 1, wherein said stabilizer is 4,4'-bis(2,6-di-tert-butylphenol).

3. The stabilized antimicrobial composition according to claim 1, wherein said stabilizer is 2,6-di-tert-butyl-p-cresol.

4. The stabilized antimicrobial composition according to claim 1, wherein said stabilizer is 2,6-di-tert-butyl-α-methoxy-p-cresol.

5. The stabilized antimicrobial composition according to claim 1, wherein said stabilizer is N-phenyl-β-naphthyl-amine.

6. The stabilized antimicrobial composition according to claim 1, wherein the concentrations of the components are: 2,2-dibromo-3-nitrilo-propionamide from about 5 to about 30 percent, water from 0 to 40%, stabilizer from 0.005 to 0.2%, and the balance to make the total of 100% being the organic solvent.

7. The stabilized antimicrobial composition according to claim 1, wherein the amount of organic solvent in the composition is from about 25% to about 75% by weight of the total antimicrobial composition.

8. The stabilized antimicrobial composition according to claim 1, wherein said composition further comprises water in amounts from about 15 to about 70% by weight of the total antimicrobial composition.

9. The stabilized antimicrobial composition according to claim 1, wherein said stabilized composition further contains an inert diluent.

10. The stabilized antimicrobial composition according to claim 9, wherein said diluent is water.

11. The stabilized antimicrobial composition according to claim 9, wherein the concentration of the 2,2-dibromo-3-nitrilo-propionamide as active ingredient is in the range of 0.5 to 500 parts per million.

* * * * *